United States Patent [19]

Jacobine et al.

[11] Patent Number: 4,764,239
[45] Date of Patent: Aug. 16, 1988

[54] SUBSTITUTED SACCHARIN COMPOUNDS AND CURABLE COMPOSITIONS CONTAINING SAME

[75] Inventors: Anthony F. Jacobine, Meriden; David M. Glaser, New Britain, both of Conn.

[73] Assignee: Loctite Corporation, Newington, Conn.

[21] Appl. No.: 899,377

[22] Filed: Aug. 4, 1986

Related U.S. Application Data

[63] Continuation-in-part of Ser. No. 758,635, Jul. 23, 1985, abandoned.

[51] Int. Cl.$^4$ ............................................. C09J 5/02
[52] U.S. Cl. ......................... 156/307.3; 252/186.26; 252/186.36; 156/326; 156/329; 526/206; 526/220; 526/227; 526/230
[58] Field of Search ........................... 526/279, 205; 252/188.31, 186.26, 186.36; 156/326, 329, 307.3

[56] References Cited

U.S. PATENT DOCUMENTS

| | | | |
|---|---|---|---|
| 2,558,139 | 6/1951 | Knock et al. | 526/220 |
| 2,833,753 | 5/1958 | Lal | 260/89.5 |
| 3,046,262 | 7/1962 | Krieble | 260/89.5 |
| 3,050,553 | 8/1962 | Novello | 260/515 |
| 3,682,875 | 8/1972 | O'Sullivan et al. | 260/89.5 |
| 3,855,040 | 12/1974 | Malofsky | 156/310 |
| 3,957,561 | 5/1976 | Skoultchi | 156/331 |
| 4,042,600 | 8/1977 | DiPippo | 260/327 |
| 4,057,555 | 11/1977 | Koike et al. | 260/301 |
| 4,090,997 | 5/1978 | Patel et al. | 260/47 |
| 4,287,330 | 9/1981 | Rich | 526/270 |
| 4,429,063 | 1/1984 | Keich | 523/176 |
| 4,443,587 | 4/1984 | Schmitt et al. | 526/146 |
| 4,447,588 | 5/1984 | Pametta | 526/301 |
| 4,513,127 | 4/1985 | Jacobine | 526/194 |

OTHER PUBLICATIONS

Chem Abstracts, vol. 86, No. 24, Jun. 14, 1977, entry 171437c.
Chem Abstracts, vol. 87, No. 21, Nov. 21, 1977, entry 168016e.
Chem Abstracts, vol. 101, No. 8, Aug. 20, 1984, entry 63707K.

Primary Examiner—Joseph L. Schofer
Assistant Examiner—Peter F. Kulkosky
Attorney, Agent, or Firm—Steven J. Hultquist

[57] ABSTRACT

A curable composition including a monomer having at least one curable acrylic functionality, an accelerator and optionally a free radical initiator, wherein the accelerator is a compound of the formula

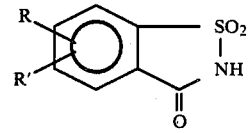

wherein R' is H or alkyl;
when R' is H, R is substituted or unsubstituted cyclohexyl, alkenylamino, or $C_3$–$C_{10}$ branched alkyl; and
when R' is alkyl, R is aralkyl.

Such compositions are useful as fixturing (e.g., thread-locking) compositions, and overcome the problems of poor solubility in organic non-polar media and temperature constraints associated with the use of saccharin per se as an accelerator in such compositions.

Also disclosed is a corresponding method of polymerizing compositions containing acrylic-functional compounds, and a method of making the substituted saccharin compounds from the corresponding substituted benzene sulfonamide.

Alkenylamido-substituted saccharin compounds and alkyl, aralkyl-disubstituted saccharin compounds are specifically disclosed.

12 Claims, No Drawings

SUBSTITUTED SACCHARIN COMPOUNDS AND CURABLE COMPOSITIONS CONTAINING SAME

This application is a continuation in part of Ser. No. 758,635, filed July 23, 1985 and now abandoned.

DESCRIPTION

1. Technical Field

This invention relates generally to saccharin derivative compounds and to compositions wherein such compounds are used as accelerators for polymerization of ethylenically unsaturated compounds.

More specifically, the invention relates to free radical curable compositions comprising polymerizable acrylic or substituted acrylic monomers in combination with free radical initiators and accelerator compounds, wherein substituted saccharin compounds are utilized as accelerators, whereby a number of deficiencies are overcome relative to use of saccharin per se in such compositions.

2. Background Art

In the art of sealants and adhesives, compositions have come into widespread use which utilize ethylenically unsaturated polymerizable monomers containing curable acrylic functionalities, the polymerization of which is free radically initiated by peroxide, perbenzoate or halogen compounds and wherein various accelerator compounds are utilized to achieve commercially viable cure times under ambient or slightly elevated temperature conditions.

Such compositions are utilized either as one-package systems, or as two-part systems in which the initiator and accelerator components are separate until mixing for final use, the accelerator having associated therewith at least part of the curable monomer. In the one-package systems, the acrylic ester compositions are oxically stabilized, i.e., the composition is stable at ambient temperatures in exposure to air or oxygen, but is curable under low oxygen conditions, preferably anoxic (anaerobic) conditions.

U.S. Pat. No. 3,046,262 to V. K. Krieble discloses anaerobic curing compositions containing acrylic ester compounds in which polymerization is initiated by organic peroxides, hydrogen peroxide, or tertiary butyl perbenzoates, and wherein the accelerator is selected from the group consisting of imides, formamide, and combinations thereof. Saccharin (benzoic sulfimide) is specifically mentioned as a suitable accelerator compounds, as is the metallic salt of such imide, sodium saccharin.

U.S. Pat. No. 2,558,139 to F. E. Knock, et al., discloses compositions suitable for dental restorations, which comprise methyl methacrylate or copolymers of methyl methacrylate, a peroxide or persulfate catalyst, and a nitrogen-containing promoter (accelerator) compound including various saccharin compounds such as chlorosaccharin, N-aceto saccharin and saccharin itself. The saccharin compounds are disclosed as species of sulfonimides of the formula

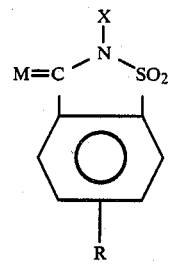

wherein M is O, S, N, R, NR or NR$_2$, wherein X is either R, COR, halogen or

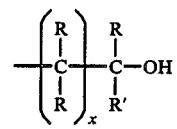

and wherein R is hydrogen, alkyl, alkenyl, alkynyl, cycloalkyl, aralkyl or aryl groups, both simple and condensed, optionally substituted with any of the radicals represented by R, NO$_2$, SO$_2$OR, SO$_2$R, NR$_2$, OCOR, OR, COOR, halogen, heterocyclic rings, SO$_2$NR$_2$,

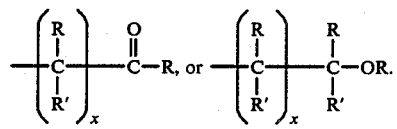

The subscript x may have the value 0 to 12.

U.S. Pat. No. 3,682,875 to D. J. O'Sullivan, et al. discloses anaerobic compositions comprising polymerizable acrylate ester polymers and peroxy polymerization initiators stabilized by incorporation therein of at least one stable nitroxide free radical as a free radical polymerization inhibitor. This patent describes the use of various polymerization accelerators in the disclosed compositions, e.g., amines and organic sulfimides. Benzoic sulfimide is specifically disclosed as a preferred accelerator component, either alone or in combination with either a heterocyclic secondary amine or a tertiary N,N-dialkyl aryl amine.

In U.S. Pat. No. 3,957,561 to M. M. Skoultchi, there are disclosed anaerobic curing compositions containing mixtures of polymerizable acrylic and substituted acrylic monomers, wherein a two-component, diazosulfone/orthosulfobenzimide catalyst system is employed. The patent indicates that the ortho-sulfobenzimide (saccharin) component may be used in its free form or in the form of the corresponding sodium salt.

In the anaerobic sealant composition disclosed in U.S. Pat. No. 4,090,997 to P. S. Patel et al., polyacrylic ester monomers are utilized in combination with an inorganic salt initiator, e.g., a persulfate or a perchlorate compound, and a polymerization accelerator which may be an organic sulfimide of a carboxylic acid. Illustrative sulfimide compounds disclosed in the patent are benzoic sulfimide (saccharin) and the sodium salt thereof.

U.S. Pat. No. 4,429,063 to K. Reich discloses anaerobically curable compositions comprising polymerizable acrylate esters or methacrylate esters and a redox system as an accelerator, which is stabilized by the addition of sulfamide derivatives containing the group

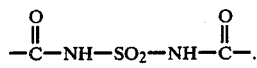

This patent also describes the use of sulfimides such as benzoic sulfimide benzosulfimide as accelerators in the disclosed compositions.

U.S. Pat. No. 4,447,588 to A. J. Rametta discloses an anaerobically curing composition comprising a polymerizable monomer, e.g., diacrylates, dimethacrylates, acrylate-terminated monomers, etc., in combination with a halogen-containing compound as a first initiator component, an organic sulfimide as a second initiator component, and a free radical polymerization inhibitor. O-benzoic sulfimide (saccharin) is disclosed to be a preferred organic sulfimide, with the organic sulfimides generally useful in the disclosed system including those of the formula

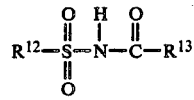

wherein $R^{12}$ and $R^{13}$ are organic radicals, preferably hydrocarbon groups containing up to about 10 carbons, and can be united to bond the sulfimide group in a heterocyclic or a polynuclear heterocyclic ring system. The patent states that $R^{12}$ and $R^{13}$ in such formula may contain any substituent which does not adversely affect the compound for its intended use as an initiator component.

In U.S. Pat. No. 4,443,587 to W. Schmitt, et al., 1,2,6-thiadiazine-3,5-dione-1,1-dioxides (malonyl sulfamides) are disclosed as polymerization accelerators for the peroxidic polymerization of ethylenically unsaturated compounds, such as methacrylic acid compounds. The patent discloses that these malonyl sulfamides may be N-substituted with cycloalkyls and that especially preferred cycloalkyls are cyclohexyl and cyclopentyl.

U.S. Pat. No. 4,513,127 to A. F. Jacobine discloses free radically curable monomer compositions comprising acrylic monomers wherein accelerator compounds of the formula

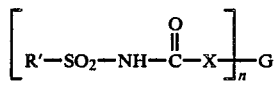

are utilized, in which G is an n valent radical providing compatibility of the accelerator with the curable monomer, X is O, O—O, S or NR"; R' is an aromatic group which may be substituted or unsubstituted; and R" is H, alkyl or aryl.

Chemical Abstracts, Vol. 101, 1984, at 101: 63707k discloses color developer compositions based on saccharin or saccharin derivatives, which are stated to be useful in thermographic recording. The disclosed saccharin compounds are of the formula

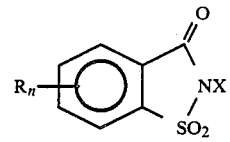

wherein R is H, $NO_2$, $NH_2$, OH, alkyl, aryl, COOH, $SO_3H$, $NR^1R^2$, $COOR^3$, $OR^4$ where $R^1$-$R^4$ are alkyl or aryl; X is H, or a group containing labile H capable of forming a stable anion; and n is between 0 and 4 inclusive.

Chemical Abstracts, Vol. 87, 1977, at 87: 168016e discloses the formation of 1,2-benzisothiazol-3-one 1,1-dioxide compounds from o-sulfobenzoic acids. The benzisothiazolone dioxide compounds are of the formula

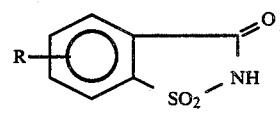

wherein R is H, Cl, Br, $NO_2$, methyl, etc.

Chemical Abstracts, Vol. 86, 1977, at 86: 171437c also describes the synthesis of 1,2-benzisothiazol-3-one 1,1-dioxide compounds, of the formula

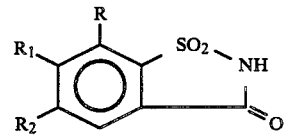

wherein R is H or methyl; $R^1$ is H, Br, Cl, F, $NO_2$, methyl, methoxy, or ethoxy; and $R^2$ is H, methyl, or methoxy.

DISCLOSURE OF INVENTION

Although the prior art variously has proposed the use of benzoic sulfimide, or saccharin, as an accelerator in curable compositions containing acrylic monomers, saccharin poses a particular problem in such use due to its very low solubility in organic non-polar media, e.g., acrylic and methacrylic ester monomers, as well as fluids such as silicones, siloxanes, silanes, and polyethylene glycol, particularly where such fluid molecules have acrylate ester end groups. This poor organic non-polar media solubility characteristic has limited the utility of saccharin in practice. Further, when saccharin is employed as an accelerator in acrylic ester compositions, limitations are imposed on permissible operating temperatures for the curable composition, due to the fact that saccharin will crystallize from the unsaturated esters (acrylates) therein at lower temperatures.

The present invention provides benzoic sulfimide compounds as accelerator components in compositions containing acrylate ester monomers, which however do not suffer the solubility disadvantages of saccharin in organic non-polar media and particularly the problem of crystallization tendencies associated with saccharin in acrylic compositions at lower temperatures.

The saccharin derivatives in the present invention are characterized by good solubility in organic non-polar media such as acrylic or methacrylic esters, relative to saccharin per se, and are stable in polymerizable compositions containing such acrylic or methacrylic esters.

In one aspect, the present invention relates to a curable composition including an ethylenically unsaturated monomer which is free radically polymerizable utilizing conventional initiators, comprising a monomer having a curable acrylic functionality of the formula

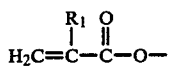

wherein $R_1$ is H or alkyl, and an accelerator compound of the formula

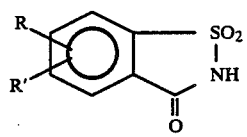

wherein R' is H or alkyl;
when R' is H, R is substituted or unsubstituted cyclohexyl, alkenylamino, or $C_3$–$C_{10}$ branched alkyl; and
when R' is alkyl, R is aralkyl.

Particularly preferred saccharin derivative compounds of the foregoing type are cyclohexyl saccharin, e.g., 5-cyclohexyl-2,3-dihydro-3-oxobenzisosulfonazole, and the branched alkyl saccharin derivatives, e.g., t-butyl saccharin. Such saccharin derivative compounds are highly soluble in organic non-polar media including acrylic and methacrylic acid esters, and have been found to be surprisingly and unexpectedly stable in (meth)acrylic ester formulations relative to corresponding formulations utilizing saccharin per se.

In another aspect, the present invention relates to a method of polymerizing ethylenically unsaturated compounds having curable acrylic functionalities of the formula

wherein $R_1$ is H or alkyl, in a composition comprising an accelerator and optionally a free radical initiator, wherein the aforementioned saccharin derivatives are utilized as the accelerator component.

Another aspect of the present invention relates to saccharin derivative compounds of the formula

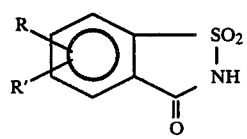

wherein R' is H or alkyl;
when R' is H, R is alkenylamido; and
when R' is alkyl, R is aralkyl.

The present invention in another aspect relates to a method of making a substituted saccharin compound from a corresponding substituted benzene sulfonamide, wherein the substituent is substituted on the benzene nucleus of the saccharin compound at the 4, 5, 6, or 7 ring position thereof, comprising the steps of:
lithiating the substituted benzene sulfonamide by reaction with an alkyl lithium compound;
contacting the reaction product with carbon dioxide;
thereafter acidifying the reaction mixture to yield an alkyl sulfonamido-substituted benzoic acid compound, wherein the carboxyl substituent of the benzoic acid compound is adjacent to the alkyl sulfonamido substituent; and
reacting the substituted benzoic acid compound with an alkyl benzène sulfonic acid monohydrate to yield the corresponding substituted saccharin compound.

A still further aspect of the invention relates to a process for making a substituted saccharin compound from a corresponding substituted benzene compound, wherein the substituent is substituted on the benzene nucleus of the saccharin compound at the 4, 5, 6 or 7 ring position thereof, comprising the steps of:
(a) reacting the substituted benzene compound with sulfuric acid to form a corresponding substituted benzene sulfonic acid;
(b) forming an alkali metal salt of the substituted benzene sulfonic acid;
(c) halogenating the alkali metal salt to form the corresponding substituted benzene sulfonyl halide;
(d) aminating the substituted benzene sulfonyl halide with a primary alkyl amine to yield a corresponding substituted benzene sulfonamide, wherein the amine nitrogen is alkyl substituted;
(e) lithiating the substituted benzene sulfonamide by reaction with an alkyl lithium compound, contacting the reaction product thereof with carbon dioxide, and thereafter acidifying the reaction mixture to yield an alkyl sulfonamido-substituted benzoic acid compound, wherein the carboxyl substituent of the benzoic acid compound is adjacent to the alkyl sulfonamido substituent; and
(f) reacting the substituted benzoic acid compound with an alkyl benzene sulfonic acid monohydrate to yield the corresponding substituted saccharin compound.

The curable compositions of the present invention comprise a polymerizable monomer having at least one acrylic functionality of the formula

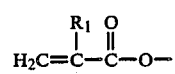

wherein $R_1$ is H or alkyl, per molecule of monomer.

Suitable monomers for employment in the compositions of the present invention include the diacrylates and dimethacrylates described in U.S. Pat. No. 3,043,820 (Kriebel), U.S. Pat. No. 3,457,212 (Fukuoka et al.), U.S. Pat. No. 3,923,737 (George et al.), and U.S. Pat. No. 3,944,521 (Bradley et al.), incorporated herein by reference. Other suitable polymerizable monomers include acrylate-terminated monomers such as the polyacrylate esters formed from organic polyisocyanates, such monomers being described, for example, in U.S. Pat. No. 3,425,988 (Gorman et al.), U.S. Pat. Nos. 4,018,352 (Baccei), 4,295,909 (Baccei), 4,309,526 (Baccei) and 4,380,613 (Nativi), all incorporated herein by reference. Particularly suitable polyfunctional acrylates and methacrylates include triethyleneglycol dimethacrylate, ethyleneglycol dimethacrylate, tetraethyleneglycol dimethacrylate, polyethyleneglycol diacrylate, polyethylene glycol dimethacrylate, 1,3-butyleneglycol dimethacrylate, trimethylolpropane trimethacrylate, neopentylglycol dimethacrylate, ethoxylated bisphenol A dimethacrylate, propoxylated bisphenol C dimethacrylate and bisphenol A bis(2-hydroxypropyl)dimethacrylate.

Monoacrylates and monomethylacrylates are also suitable for employment in the compositions of the present invention as the polymerizable monomer. Suitable monoacrylates and monomethylacrylates include cyclohexyl methacrylate, 2-ethylhexyl methacrylate, hydroxyethyl methacrylate, isooctyl acrylates and n-butyl acrylate.

Methacrylic acid, acrylic acid, and similar alpha, beta-unsaturated carboxylic acids are also suitable for employment as polymerizable monomers in the compositions of the present invention as are half-esters of maleic acid. Other suitable half-esters include those described in U.S. Pat. No. 3,428,614 (Brownstein) and U.S. Pat. No. 4,080,238 (Wolinski et al.), incorporated herein by reference.

Poly(methyl)acrylate functional reaction products of the aforementioned half-esters are also useful, such as those described in U.S. Pat. No. 4,209,604 (Weber), incorporated herein by reference.

Still other suitable monomers include the (meth)acrylate functional phosphorous containing monomers described in U.S. Pat. Nos. 4,044,044 (Saito), 4,259,117 (Yamauchi et al.), 4,434,278 (Skiscim) and 4,442,239 (Tsunekawa).

Acrylic and methacrylic functional silanes, siloxanes and silicones are yet another class of polymerizable monomers useful in the inventive compositions. Silicones of such type are disclosed in U.S. Pat. Nos. 2,793,223; 2,898,361; 2,922,806; 2,956,044; 3,878,263; 4,035,355; and 4,348,454, all incorporated herein by reference, and in copending applications Ser. Nos. 623,759 (Nakos et al), 623,760 (Klemarczyk, et al.) and 623,791 (Lin), filed June 22, 1984, all incorporated herein by reference. Although anaerobic acrylic silicone formulations have been previously demonstrated in laboratory experiments using suspended saccharin, the insolubility of saccharin in these silicones has been a major factor preventing realization of a practical and commercially acceptable anaerobic silicone formulation, and this deficiency is overcome by the use of the saccharin derivative compounds of the present invention.

In order to enhance the shelf-life of the compositions of the present invention it may be desirable to remove metal ions, if such are present, from the polymerizable monomer. This may be particularly desirable in the event that commercially-obtained monomers, which often contain significant amounts of metal ions, are employed in these compositions. Removal of metal ions may be effected by means known to those skilled in the art.

The compositions of the present invention may comprise a single type of polymerizable monomer or may comprise a blend of two or more different polymerizable monomers.

The compositions of the invention further may optionally comprise, or alternatively, in use may be combined with, an effective amount of an initiator of polymerization such as those selected from the class of hydroperoxides, of which cumene hydroperoxide and t-butyl hydroperoxide are examples; peroxyesters, such as t-butyl perbenzoate, benzophenone peroxyesters and similar peroxyesters described in U.S. Pat. No. 4,416,826 (Neckers), incorporated herein by reference, and the fluorenone peroxyesters described in copending application Ser. No. 564,150, filed Dec. 22, 1983 (Humphreys), also incorporated herein by reference; peroxy carbamates (i.e., reaction products of hydroperoxides and isocyanates); and certain halogen containing compounds having electronic structures which facilitate free radical formation, the compounds being defined by the formula:

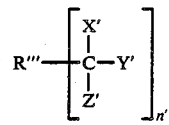

wherein:
X' is selected from the group consisting of H, CH$_3$, Cl, and Br;
Y' and Z' are each selected independently from the group consisting of Cl and Br;
R''' is selected from the group consisting of aromatic and heteroaromatic residues; and
n' is an integer from 1 to 3 inclusive.

These halogen-containing compounds are exemplified and described in greater detail in U.S. Pat. No. 4,447,588, incorporated herein by reference.

Typically the initiator component will be utilized in an amount of 0.5–10 parts by weight per 100 parts of the monomer component.

Of the various classes of initiators described above, the peroxy initiators are generally preferred over the halogenated compounds, with the hydroperoxides generally being the most preferred.

The accelerators useful in the broad practice of the present invention are those of the formula

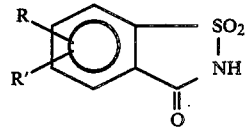

wherein R' is H or alkyl;
when R' is H, R is substituted or unsubstituted cyclohexyl, alkenylamino, or C$_3$–C$_{10}$ branched alkyl; and
when R' is alkyl, R is aralkyl.

Among the preferred accelerator compounds defined by the above formula are those wherein R' is H and R is C$_3$–C$_{10}$ branched alkyl, most preferably those in which R' is H and R is C$_3$–C$_6$, e.g., isopropyl saccharin, and t-butyl saccharin.

In such branched alkyl saccharin compounds, the carbon number of the branched alkyl substituent, should not generally exceed 10, since at higher carbon numbers, the temperature stability and accelerative activity of the saccharin derivative in the acrylic monomer composition tend to diminish to unsuitably low values.

Another particularly advantageous accelerator compound among those defined by the above formula is the compound wherein R' is H and R is cyclohexyl. Although the cyclohexyl radical may be substituted on the benzene nucleus at the 4, 5, 6, or 7 ring position thereof, a preferred compound has the cyclohexyl radical attached to the 5 carbon position of the benzene ring, as 5-cyclohexyl-2,3-dihydro-3-oxobenzisosulfonazole.

Other highly useful accelerator compounds among those defined by the above formula are those wherein R' is H, and R is either (meth)acrylamido or undecenamido, and those derivatives wherein R' is alkyl, e.g., methyl, and R is aralkyl, e.g., benzyl.

The various substituents on the benzene nucleus of the saccharin derivative compounds of the present invention, e.g., cyclohexyl, alkenylamino, $C_3-C_{10}$ branched alkyl, or aralkyl in the case of R, and alkyl in the case of R', may themselves be substituted or unsubstituted. When these radicals are substituted, it is to be understood that any substituent which does not adversely affect the saccharin derivative compound for its exemplary use as an accelerator in the compositions of the present invention, may be substituted on such radicals.

Among all of the aforementioned saccharin derivative compounds potentially useful in the present invention, cyclohexyl saccharin is preferred, and the $C_3-C_{10}$ branched alkyl saccharin compounds are most preferred, relative to saccharin per se, due to their respectively greater solubilities in organic non-polar media such as (meth)acrylic ester monomers.

The use of the saccharin derivatives of the present invention overcomes the limitations otherwise imposed by saccharin on permissible operating temperatures for curable (meth)acrylic ester compositions, due to the tendency of saccharin to crystallize from such unsaturated esters at relatively lower temperatures.

Illustrative of the utility of the preferred $C_3-C_{10}$ branched alkyl and cyclohexyl saccharin compounds is their solubility in acrylate ester compounds, e.g., those formed by diol-capped siloxanes of the formula

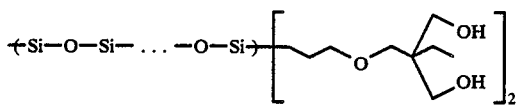

when reacted with methacrylate compounds such as isocyanato ethyl methacrylate to yield siloxane compounds having terminal groups thereon of the formula

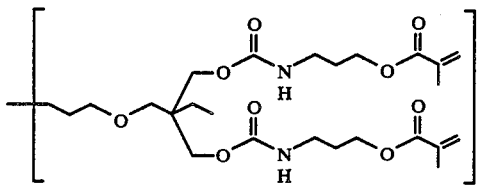

This acrylic ester monomer, in which saccharin is substantially insoluble, readily dissolves the preferred $C_3-C_{10}$ branched alkyl and cyclohexyl saccharin compounds of the present invention, particularly in instances where the precursor siloxanes are of lower molecular weights, on the order of 5,000 and below. As a further example, in polyethylene glycol dimethacrylate, wherein saccharin is only sparingly soluble, cyclohexyl saccharin is readily soluble up to levels in excess of 15% by weight, and t-butyl saccharin is readily soluble at levels up to 23% by weight.

In addition, it has been found quite unexpectedly that acrylate ester formulations containing the saccharin derivative compounds of the present invention, particularly cyclohexyl saccharin or branched alkyl saccharin, exhibit extremely high stabilities (measured as storage time until gelation) relative to corresponding saccharin formulations.

In general, the accelerator compounds of the present invention may be employed at any suitable concentration which is effective to provide curing of the polymerizable monomer in the formulations in which such compounds are utilized.

As indicated, one advantage of the saccharin derivatives of the present invention is that they are highly soluble in a number of monomeric formulations where saccharin has not been able to be usefully employed as a result of its low solubility.

In those formulations where saccharin has conventionally been employed as an accelerator, the saccharin derivatives of the present invention may be employed in place thereof.

In either case, the appropriate concentration of the saccharin derivative in the specific formulation may readily be determined by those skilled in the art, without undue experimentation.

By way of example, t-butyl saccharin may be utilized in various acrylic monomer formulations at levels up to in excess of 20% by weight, with levels on the order of 1-15% generally being preferred and 2-12% being most preferred. Cyclohexyl saccharin, as another example, is useful in various acrylic monomer formulations at levels up to in excess of 15%, with levels on the order of 1-13% generally being preferred and 2-10% being most preferred. These weight % values are based on the weight of the polymerizable monomer for which the accelerator is effective in the formulation.

In those instances in which preferred saccharin derivatives such as t-butyl saccharin and cyclohexyl saccharin have been employed in place of saccharin in formulations normally using saccharin, it has generally been satisfactory to utilize concentrations of the saccharin derivatives providing from about 1.5 to about 6.0 saccharin equivalents in the formulation. It will be appreciated, however, that other and different saccharin equivalents levels may be utilized to good advantage in specific formulations, depending on the composition and curing characteristics desired.

The inventive compositions may optionally include additional co-accelerator ingredients. Especially preferred are tertiary aromatic amines, particularly N,N-dimethyl-p-toluidine, N,N-diethyl-p-toluidine and N,N-dimethyl aniline. Other classes of co-accelerators are the hydrazine derivatives, such as 1-acetyl-2-phenylhydrazine, described in U.S. Pat. No. 4,287,330, incorporated herein by reference, and ferrocene or substituted ferrocene compounds as described in U.S. Pat. No. 3,885,040, also incorporated herein by reference.

Generally, when the compositions of the present invention as initially made incorporate a polymerization initiator, the compositions may also suitably include an inhibitor of polymerization in an amount effective to give desired shelf stability to the composition. Suitable inhibitors are well known to those skilled in the art and include those disclosed in the aforementioned patents which describe anaerobic compositions. Metal chelators, such as ethylenediaminetetraacetate (EDTA) and 1-hydroxyethylidine-1,1-diphosphonic acid (HEDPA), and quinone type inhibitors, such as hydroquinone, methyl hydroquinone, naphthaquinone and benzoquinone, are preferred.

It is contemplated that the inventive compositions comprising polymerizable acrylic monomers, a polymerization initiator, inhibitor and an accelerator, will be most useful as low oxygen curing (anaerobic) compositions. Anaerobic compositions are formulated so that the initiator, accelerator and inhibitor are balanced to give compositions which are stable when in contact with air (oxygen) but which readily polymerize when deprived of oxygen, such as when a composition coated bolt is mated with a nut or when the composition is drawn into the microscopic pores of a metal casting.

It is also contemplated, however, that compositions of the invention may usefully be formulated as two liquid formulations (two-package systems) in which some or all of the accelerator system is kept separate from the initiator until just before use. Contact or mixing of the initiator-containing liquid and the accelerator-containing liquid results in rapid polymerization which, in some cases, may not be preventable by exposure to oxygen. Examples of such two liquid compositions are contained in U.S. Pat. Nos. 4,442,267 (Charnock), 4,451,615 (Charnock) and U.K. published application No. 2121811A, all incorporated herein by reference. When formulating compositions of the invention by reference to these anaerobic and two liquid patents, saccharin derivative accelerators of the present invention may generally be substituted for saccharin in the example formulations of these patents, as previously indicated, to obtain substantially similar results.

The invention is further illustrated by the following examples, wherein all parts and percentages are by weight unless otherwise noted. Examples I-V are illustrative of the synthesis of the method of the present invention for making a substituted saccharin compound from a corresponding substituted benzene compound. Specifically, Examples I-V illustrate the formation of 5-cyclohexyl saccharin (5-cyclohexyl-2,3-dihydro-3-oxobenzisosulfonazole) from cyclohexyl benzene.

EXAMPLE I

4-Cyclohexylbenzenesulfonic Acid Sodium Salt

Cyclohexyl benzene (500 gm, 3.12M) is stirred in a five liter 3-necked flask equipped with a condenser and a thermowatch, and is warmed to 70° C. Sulfuric acid (381 gm, 3.74M) and 30% oleum (38.2 gm) are added dropwise to the stirred reaction at a rate sufficient to maintain a temperature of approximately 70°-75° C. When the addition is complete, the reaction is aged at 70° C. for three hours and then cooled. The resulting reaction mixture, which is deep red in color, then is drowned in two liters of a saturated NaCl solution that is cooled to approximately 5° C. The solid precipitated in the salt solution then is filtered and washed with hexane, following which the precipitate is dried in a vacuum oven at 75° C.

EXAMPLE II

4-Cyclohexylbenzenesulfonyl Chloride

The sodium salt prepared in Example I (420 gm, 1.6M) is intermittently mixed with phosphorous pentachloride (160 gm, 0.77M) in a three liter multi-necked flask and slowly warmed to 70° C. in an oil bath. The liquified reaction mass is aged at 70° C. for 8 hours, then cooled to room temperature and carefully poured over one kilogram of cracked ice. A solid precipitate is removed by filtration and the aqueous phase is extracted with methylene chloride three times, each time using 300 milliliters of MeCl. The combined organic phases are dried and concentrated using a rotary evaporator. 4-cyclohexylbenzenesulfonyl chloride (338 gm, 81% of theoretical yield) was recovered as a crude product.

EXAMPLE III

N-t-Butyl-4-Cyclohexylbenzenesulfonamide

The sulfonyl chloride compound obtained in Example II (338 gm, 1.3M) is suspended in dry dioxane (400 ml) under argon atmosphere in a four-necked round-bottomed flask equipped with a condenser, a thermowatch and à constant pressure addition funnel. Excess t-butylamine (210 gm, 2.78M) is added drop-wise and the temperature of the reaction mixture is allowed to increase to approximately 60°-70° C. When the addition of amine is complete, the reaction mixture is aged at 70° C. for one hour, then cooled to 30° C. and the amine hydrochloride salt is removed by filtration. Concentration of the filtrate yields the crude sulfonamide. Nmr spectra obtained on a Varian EM-360 MHz nmr spectrometer, recorded in ppm downfield from tetramethylsilane, and infrared spectra recorded on a Nicolet MX-1 Fourier Transform infrared spectrometer provides spectral data consistent with the expected structure.

EXAMPLE IV 2-(t-Butylsulfonamido)-5-Cyclohexylbenzoic Acid

The sulfonamide product of Example II (227 gm, 0.77M) is dissolved in dry tetrahydrofuran and stirred under argon atmosphere at $-15°$ C. N-butyllithium (2.0M, 750 ml) was added drop-wise at a rate sufficient to maintain a temperature of $-5°$ to 0° C. When all butyllithium is added, the reaction mixture is allowed to warm to room temperature and is stirred for at least two hours. After evolution of hydrogen ceases, the reaction mixture is rapidly poured over a large excess of carbon dioxide. When the reaction mixture thereafter warms to room temperature, the slurry is acidified to a pH of about 3, with dilute hydrochloric acid. The tetrahydrofuran layer is separated and concentrated to yield the benzoic acid. Spectral data (IR, C=O 1711 cm$^{-1}$; nmr N—H, Ca=6-7 ppm) are consistent with the anticipated structure.

EXAMPLE V

5-Cyclohexyl Saccharin

The sulfonamido benzoic acid obtained from Example IV is stirred in toluene under argon atmosphere in a flask equipped with a Dean-Strark trap. Toluenesulfonic acid monohydrate (5 mol%) is added and the reaction mixture is warmed to reflux. When no further co-distillation of water is observed, the reaction mixture is cooled to room temperature and concentrated using a rotary evaporator. The resulting crude semi-solid oil is dissolved in a minimum amount of ethyl acetate at the boiling point and the resulting solution then is made cloudy by the addition of hexane. The desired cyclohexyl saccharin compound crystallizes on cooling. The dissolution and crystallization procedure may be repeated if higher purity material is desired. Spectral data for the crystallized product (IR, C=O 1720 cm$^{-1}$; nmr delta=1-2.2 m cyclohexyl, delta=6.2 s broad N—H, delta=7-8 m aromatic) are consistent with the anticipated structure of 5-cyclohexyl saccharin.

EXAMPLE VI

In this example, a standard thread-locking formulation curable under low oxygen conditions, preferably anaerobic conditions, was formulated with the composition shown in Table I below.

TABLE I

| Component | Amount |
|---|---|
| Polyethylene glycol dimethacrylate | 19.06 gm. |
| Cumene hydroperoxide | 0.4 gm. |
| Amine[1] | 0.2 gm. |
| Stabilizer[2] | 1 drop |
| Stabilizer[3] | 5 drops |
| Accelerator | As listed in Table II |

[1] N,N—diethyl-p-toluidine/N,N—dimethyl-o-toluidine 2:1 by weight.
[2] 5% naphthaquinone solution
[3] 9% sodium EDTA in methanol Formulations were then made up based on the composition of Table I, using the accelerators in Table II at the concentrations identified therein (% by weight, based on the acrylate ester). The substrates were black phosphate and oil bolts. Nuts were degreased with methylene chloride. The nut and bolt substrates to which thread-locking formulations had been applied were cured overnight. The break and prevail values were determined by application of torque to the fixtured nut/bolt assembly, with the break value representing the force necessary to break the adhesive bond of the fixture, and the prevail value representing the force necessary to continue removal of the nut from the bolt after the adhesive bond of the fixture has been broken. Break and prevail values are set forth in Table II in units of inch-pounds, along with (parenthetically) the corresponding metric values, in joules. The break/prevail values are averages for three specimens of each sample.

TABLE II

| Sample No. | Accelerator | Concentration, wt % | Break/Prevail, in.-lbs. (joules) |
|---|---|---|---|
| 1 | 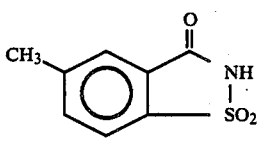 | 1.5 | 260/340 (29.4/38.4) |
| 2 | 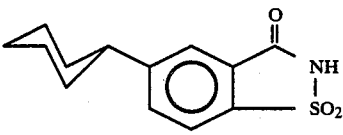 | 3.0 | 248/295 (28.0/33.3) |
| 3 | 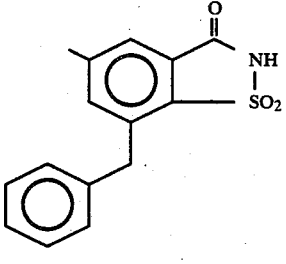 | 4.5 | 213/233 (24.1/26.3) |
| 4 | 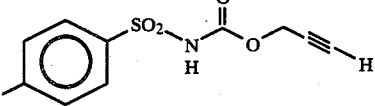 | 2.5 | 207/200 (23.4/22.6) |
| 5 | 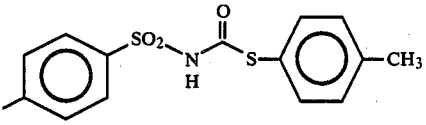 | 4.5 | 233/323 (26.3/36.5) |
| 6 | 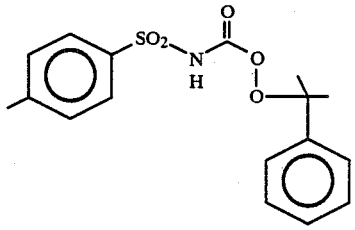 | 7 | 206/302 (23.3/34.1) |

| Sample No. | Accelerator | Concentration, wt % | Break/Prevail, in.-lbs. (joules) |
|---|---|---|---|
| 7 | (structure: benzene ring with C(=O)NH-SO2) | — | 306/320 (34.6/36.2) |

EXAMPLE VII

In this example, a curable acrylate formulation (Formulation A) was made up in accordance with the composition set out in Table III below.

TABLE III

| Component | Amount |
|---|---|
| Polyethylene glycol dimethacrylate | 300.0 gm. |
| Amine[1] | 3.06 gm. |
| Cumene hydroperoxide | 6.12 gm. |
| Stabilizer[2] | .612 gm. |
| Stabilizer[3] | 3.06 gm. |
| Accelerator | As shown in Table IV |

[1] N,N—diethyl-p-toluidine/N,N—dimethyl-o-toluidine, 2:1 by weight
[2] 5% naphthaquinone solution
[3] 9% NaEDTA in methanol Samples 8–13 then were made up using Formulation A and saccharin or 5-cyclohexyl saccharin as accelerators, in the amounts set out in Table IV below. The compositions including the accelerators were applied to substrates of grade #2 steel nuts and bolts, ⅜ inch (0.95 cm.), 16, degreased with methylene chloride. Fixture times in minutes (except where otherwise noted for sample 13) were measured. In addition, corresponding quantities of the respective sample 8–13 compositions were stored under 82° C. oven conditions to evaluate their stability, with the time until gelation being measured for each sample composition, as set out in Table IV below.

TABLE IV

| Sample | 8 | 9 | 10 | 11 | 12 | 13 |
|---|---|---|---|---|---|---|
| Composition | | | | | | |
| Formulation A | 50 | 50 | 50 | 50 | 50 | 50 |
| Saccharin | .75 | 2.25 | — | — | — | — |
| 5-Cyclohexyl-Saccharin | — | — | 1.09 | 3.2 | 6.54 | — |
| mmoles Accelerator | 4.1 | 12.3 | 4.1 | 12.1 | 24.8 | — |
| Performance | | | | | | |
| Fixture Time, min. ± 2 | 6.5 | 7 | 11 | 10 | 9 | (2 hr., no fixture) |
| 82° C. Stability Time to Gelation, hrs. | 1-2 | 1-2 | 72 | 72 | 8 | 48 |

EXAMPLE VIII

In this example, various thread-locking compositions were made up using a modification of Formulation A of Example VII, wherein the sodium EDTA stabilizer was deleted from the formulation as initially made up. In all other respects, this formulation (Formulation B) was the same as Formulation A utilized in Example VII. The fixture times were measured on grade #2, ⅜ inch (0.95 cm.), 16 steel nuts and bolts, degreased with methylene chloride, and also on sand-blasted steel, as noted. 82° C. stability was measured for each of the samples.

The specific compositions of samples 14–17 and their performance data are set forth in Table V below.

TABLE V

| | Samples | | | |
|---|---|---|---|---|
| Component | 14 | 15 | 16 | 17 |
| Formulation B | 50 | 50 | 50 | 50 |
| Saccharin | .75 | — | — | — |
| Cyclohexyl Saccharin | — | 1.09 | 2.28 | — |
| Stabilizer[1] | .51 | .51 | .51 | .51 |
| Performance | | | | |
| Fixture Time On Nuts and Bolts, Min. ± 2 | 7 | 7 | 6 | negligible after 1 hour |
| Fixture Time On Sand-Blasted Steel, Min. ± 2 | 25–30 | 30–45 | 40–45 | — |
| 82° C. Stability, hours | 26 | 72 | 72 | 44 |

[1] 9% Sodium EDTA in methanol

EXAMPLE IX

Oxidation of 2-methyl-5-nitrobenzenesulfonamide was carried out resulting in 69% conversion to 6-nitrosaccharin. Catalytic reduction with palladium on carbon gave the corresponding aminosaccharin of high purity in 80–90% yield. Functionalization of the amino group of this aminosaccharin with acyl chlorides and pyridine gave the corresponding amides from methacrylic acid and undecylenic acid.

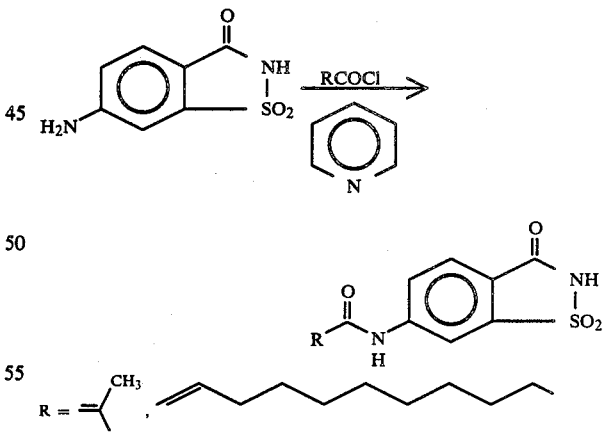

EXAMPLE X

N-t-butylbenzenesulfonamide was lithiated in tetrahydrofuran at a temperature of −10° C. to −25° C. for two hours with n-butyl lithium to form the corresponding lithiated compound. The lithiated compound then was alkylated by alkyl halides (iodides and bromides) at 50° C. to yield the corresponding benzenesulfonamides. The bromide alkylation reaction was found to be slower than the iodide reaction, but the former may be catalyzed with crown ethers to achieve suitable reaction rates.

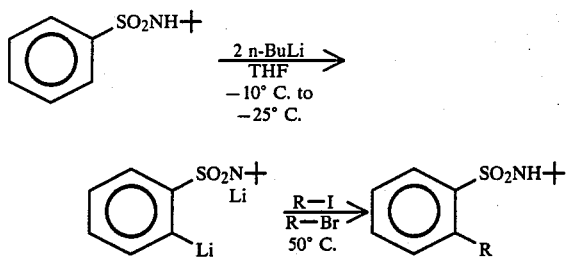

By this method, 2-ethyl and 2-N-octyl benzenesulfonamides were prepared. Carbonation of these materials, as in Example IV, then may be carried out to yield the corresponding saccharin derivatives.

EXAMPLE XI

N-t-butyl sulfonamidobenzoic acid, precursor to benzylmethyl saccharin was prepared by lithiation of the benzene-t-butylsulfonamide and alkylation with benzaldehyde, followed by hydrogenolysis over palladium and subsequent lithiation and carbonation. This precursor was refluxed in the presence of para-toluenesulfonic acid. The product isolated from the reaction mixture gave an nmr spectrum which showed no alkyl (t-butyl) groups from the precursor (1) to be present; the spectrum was otherwise consistent with a cyclized product, of the structure (2) shown below.

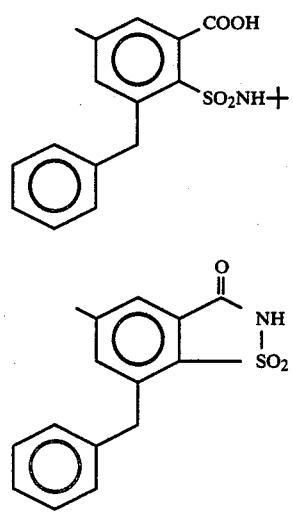

EXAMPLE XII

The cyclohexyl and benzylmethyl saccharin compounds of Examples V and XI, as well as 5-methylsaccharin, were tested for solubility in polyethylene glycol dimethacrylate (PEGMA), in comparison to saccharin. All of such saccharin derivatives exhibited accelerative activity and were more soluble in the acrylate system than saccharin. Formulations were made up for each accelerator, of PEGMA, initiator and the accelerator, and the respective formulations were evaluated as to their ultimate strengths as thread-lockers. All of the aforementioned saccharin derivatives gave ultimate strengths which were of the order of magnitude of the strengths achieved using saccharin, being lower in value than the saccharin formulations by approximately 25–40%.

EXAMPLE XIII

Accelerative activity for undecenamido saccharin was measured against saccharin, in acrylic formulations. Fixture times for the formulation containing the saccharin derivative were generally higher, on the order of 17–20 minutes, versus 7–10 minutes for saccharin-containing formulations. Ultimate strengths as thread-lockers were evaluated, and the strength values for the formulation containing undecenamido saccharin though generally lower than the corresponding saccharin-containing formulation, in all cases approached those obtainable with saccharin.

EXAMPLE XIV 5-cyclohexylsaccharin was synthesized and evaluated against saccharin for solubility in polyethylene glycol dimethacrylate (PEGMA). 5-cyclohexylsaccharin had a measured solubility of 17.5 weight percent in PEGMA, versus 4.5 weight percent for saccharin therein.

EXAMPLE XV

In this example, the solubilites of 4-t-butyl saccharin, 5-cyclohexyl saccharin, and saccharin were comparatively evaluated in the PEGMA acrylic monomer. The evaluation procedure for each of these accelerator compounds is described below.

4-t-Butyl Saccharin 5 gm of PEGMA and 1.06 gm of 4-t-butyl saccharin ("TBS") were introduced to a 50 ml round bottom flask having a magnetic stirrer bar therein. The flask then was placed on a rotary evaporator unit and rotated to mix the flask contents. All TBS solids dissolved within 5 minutes, yielding a solution containing 17.5% by weight of TBS. 0.61 gm additional TBS then was added to the solution, to provide a 25% by weight concentration of TBS in the PEGMA. Mixing of the flask contents was carried out as previously, but the solids were incompletely dissolved after 1 hour. 0.6 gm of PEGMA then was added to the flask, reducing the TBS concentration to 23% by weight. Subsequent mixing resulted in dissolution of all TBS solids at the 23% concentration.

5-Cyclohexyl Saccharin 5 gm of PEGMA and 1.06 gm of 5-cyclohexyl saccharin ("CHS") were introduced to a 50 ml round bottom flask and subjected to mixing on the rotary evaporator unit as in the case of TBS. Approximately 1 hour was required to break up large crystals of the CHS and achieve complete dissolution. 0.19 gm of CHS then was added to the solution and subjected to mixing for 2 hours without dissolution. The flask was left overnight, but solids were present the next day, and persisted even after further mixing. 1.3 gm of PEGMA were added, to yield a concentration of CHS therein of 17% by weight, and all solids dissolved. 0.9 gm of additional CHS was added, to establish a CHS concentration of 18% by weight, and all CHS solids were dissolved at this concentration.

Saccharin 10 gm of PEGMA and 0.52 gm of saccharin were placed into a 50 ml round bottom flask and subjected to mixing in the manner of the preceding accelerator compounds. After 1.5 hours of mixing, solids were still present. 1.04 gm of PEGMA then were added, to establish a saccharin concentration of 4.5% by weight, and at this concentration all saccharin solids were borderline soluble, thus establishing this concentration as the practical maximum for solubility of saccharin in PEGMA.

EXAMPLE XVI

In this example, a curable acrylate formulation was made up, using the composition set forth in Table VI below.

TABLE VI

| Component | Amount |
|---|---|
| Polyethylene glycol dimethacrylate | 500 gm. |
| Cumene hydroperoxide | 10.02 gm. |
| Amine (same as Example VI) | 5.10 gm. |
| Stabilizer[2] | 1.02 gm. |
| Stabilizer[3] | .59 gm. |

[2,3] these are the same stabilizers, respectively, as the stabilizers identified by the same superscript designations in Example VI The above formulation (Formulation C) then was employed to make Samples 18–21 having the compositions shown in Table VII below, wherein saccharin, 4-t-butyl saccharin, and 5-cyclohexyl saccharin were variously used as accelerators. Fixturing properties then were evaluated by applying the compositions including the accelerators to substrates of grade #2 steel nuts and bolts, ⅜ inch (0.95 cm.), 16, degreased with methylene chloride. Fixture times in minutes were measured for the various samples. In addition, fixturing was evaluated on steel lap panels at zero gap, with the fixturing time in minutes again being measured. The fixturing data are shown in Table VII below.

TABLE VII

| Sample | 18 | 19 | 20 | 21 |
|---|---|---|---|---|
| Composition | | | | |
| Formulation C | 50 | 50 | 50 | 50 |
| Saccharin | .75 | — | — | — |
| t-butyl saccharin | — | .98 | 1.47 | — |
| cyclohexyl saccharin | — | — | — | 1.09 |
| Fixture Times, minutes | | | | |
| ⅜ inch (.95 cm.), 16, nuts and bolts | 13.5 | 16 | 18.5 | 18 |
| steel laps, 0 gap | 17.5 | 19.5 | 16.5 | 18.5 |

EXAMPLE XVII

The 82° C. temperature stability was determined for samples 18–21, and a further sample 22, identical to sample 21 but with 1.64 gm of cyclohexyl saccharin in place of the 1.09 gm used in sample 21.

An equal amount of each of the samples 18–22 was placed in test tubes. The test tubes were then placed in a constant temperature 82° C. water bath, and the samples monitored at regular intervals to determine the time to gellation for each sample. The results are set out in Table VIII below.

TABLE VIII

| Sample | Time Until Gellation Occurred |
|---|---|
| 18 | 6.5 hours |
| 19 | 6.5 hours |
| 20 | greater than 3 days |
| 21 | 4.5 hours |
| 22 | 4.5 hours |

EXAMPLE XVIII

In this example, the fixturing properties were determined for samples 23–28, based on Formulation C as described in Example XVII, but with the accelerator compounds as set forth in Table IX below.

Fixturing times, in minutes, then were determined for the sample compositions on substrates of grade #2 steel nuts and bolts, ⅜ inch (0.95 cm.), 16, degreased with methylene chloride. Data are set forth in Table IX.

TABLE IX

| Sample | 23 | 24 | 25 | 26 | 27 | 28 |
|---|---|---|---|---|---|---|
| Composition | | | | | | |
| Formulation C | 19.9 | 19.9 | 19.9 | 19.9 | 19.9 | 19.9 |
| saccharin | .30 | — | — | — | 0.60 | — |
| 6-amino saccharin | — | .325 | — | — | — | — |
| 6-undecenamido saccharin | — | — | .597 | 1.19 | — | 2.38 |
| Fixture Times, minutes | | | | | | |
| Grade #2 Nuts and Bolts | 10 | * | 17 | 25 | 7 | approx. 40 min. |

*negligible fixturing at 40 minutes

The foregoing examples thus show that the substituted saccharin compounds of the present invention have substantially improved solubility in organic non-polar media such as acrylic and methacrylic esters, and that t-butyl saccharin and cyclohexylsaccharin in particular exhibit unexpectedly high stability, as indicated by the aforementioned 82° C. stability tests in comparison to corresponding formulations containing saccharin.

BEST MODE FOR CARRYING OUT THE INVENTION

The best mode of practicing the present invention involves the use of t-butyl saccharin as a polymerization accelerator in the acrylic monomer formulations described herein, as in Sample 20. The specific Sample 20 composition has an 82° C. stability which is in excess of three days, and provides fixturing times which are on the order of those characteristic of formulations wherein saccharin is employed as the accelerator (see Example XVI). As indicated, the solubility of t-butyl saccharin in acrylic monomers such as PEGMA is substantially higher than the solubility levels achieveable by saccharin per se (see Example XV).

The t-butyl saccharin compound may readily be made in a manner analogous to the method described in Examples I–V herein for the synthesis of cyclohexyl saccharin, starting with t-butyl benzene.

The t-butyl saccharin-containing formulations, such as that of Sample 20 in Example XVI, are best employed as fixturing compositions curable under low oxygen, preferably anoxic, conditions.

INDUSTRIAL APPLICABILITY

The compositions of the present invention have broad applicability for high-strength adhesive bonding of substrates such as metal surfaces. A specific preferred application is as thread-locking compositions which may be applied to the threading surfaces of nut and/or bolt elements. The mating of the nut and bolt elements having the composition applied thereto results in the composition being deprived of contact with oxygen so that curing of the polymerizable monomer in the composition is effected.

As a result, such fastening elements are strongly fixtured, and provide a high level of structural integrity to assemblies and constructions in which they are employed.

What is claimed is:

1. A composition of improved 82° C. stability to gellation, which is stable in the presence of oxygen and curable when deprived of oxygen, comprising:
   (a) a monomer having at least one curable acrylic functionality of the formula

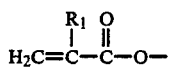

wherein $R_1$ is H or alkyl;
   (b) a saccharin derivative accelerator compound having higher solubility than saccharin in said monomer, of the formula

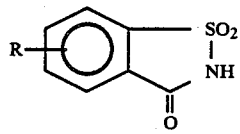

wherein R is cyclohexyl or t-butyl;
   (c) a co-accelerator selected form the group consisting of:
      (i) tertiary aromatic amines;
      (ii) compounds of the formula

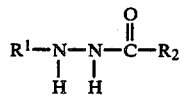

wherein $R^1$ is phenyl substituted with $C_1$–$C_{14}$ alkyl group and $R^2$ is selected from the group consisting of hydrogen, alkyl, cycloalkyl, alkenyl, cycloalkenyl, aryl, alkoxy, aryloxy, carbonyl, amino, and the following groups:

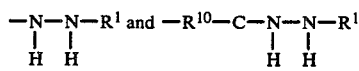

wherein $R^{10}$ is selected from the group consisting of alkyl groups containing one to about 10 carbon atoms, alkenyl groups containing two to about 10 carbon atoms, and aryl groups containing up to about 10 carbon atoms; and
      (iii) an organic compound containing a ferrocene moiety; and
   (d) a free radical initiator selected from hydroperoxides, peroxyesters, peroxycarbamates, and halogen containing compounds defined by the formula

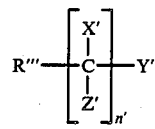

wherein X' is selected from H, CH$_3$, Cl, and Br; Y' and Z' are each selected independently from the group consisting of Cl and Br; R''' is selected from the group consisting of aromatic and heteroaromatic residues; and n' is an integer from 1 to 3 inclusive.

2. A curable composition according to claim 1 wherein R is cyclohexyl.

3. A composition according to claim 1 wherein the accelerator is 5-cyclohexyl-2,3-dihydro-3-oxobenzisosulfonazole.

4. A curable composition according to claim 1 wherein R is t-butyl.

5. A curable composition according to claim 1 wherein the monomer is an acrylic or methacrylic functional silane, siloxane or silicone.

6. A curable composition according to claim 1 wherein the monomer is a siloxane having terminal end groups of the formula

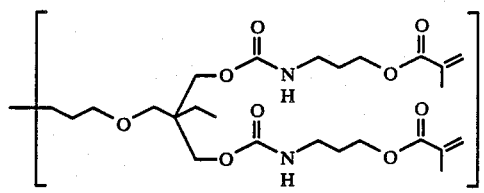

7. A curable composition according to claim 1 wherein the monomer is polyethylene glycol dimethacrylate.

8. A curable composition according to claim 1 wherein the free radical initiator comprises cumene hydroperoxide.

9. A composition according to claim 1, comprising a polymerization inhibitor.

10. A composition according to claim 9, wherein said polymerization inhibitor is selected from the group consisting of metal chelate and quinone compounds.

11. A composition of improved 82° C. stability to gellation, which is stable in the presence of oxygen and curable when deprived of oxygen, comprising:
   (a) a monomer having at least one curable acrylic functionality of the formula

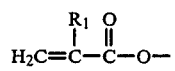

wherein $R_1$ is H or alkyl;
   (b) a saccharin derivative accelerator compound having higher solubility than saccharin in said monomer, of the formula

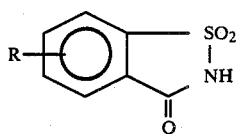

wherein R is cyclohexyl or t-butyl;

(c) a tertiary aromatic amine co-accelerator; and
(d) a free radical initiator selected from hydroperoxides and peroxyesters.

12. A method of adhesive bonding of substrates to one another, by applying to at least one of said substrates a composition according to claim 1, placing said substrates in bonding relationship to one another, and curing said composition in the substantial absence of oxygen.

* * * * *

UNITED STATES PATENT AND TRADEMARK OFFICE
CERTIFICATE OF CORRECTION

PATENT NO. : 4,764,239

DATED : August 16, 1988

INVENTOR(S) : Anthony F. Jacobine, et al

It is certified that error appears in the above-identified patent and that said Letters Patent is hereby corrected as shown below:

Column 1, lines 55-56, change "compounds" to --compound--.

Column 3, line 61, change "R'is" to --R' is--.

Column 5, line 31, after "e.g.," and before "5," delete the extra spaces.

Signed and Sealed this

Third Day of January, 1989

*Attest:*

DONALD J. QUIGG

*Attesting Officer*  *Commissioner of Patents and Trademarks*